United States Patent [19]
Fillon, Jr.

[11] Patent Number: 6,056,249
[45] Date of Patent: May 2, 2000

[54] DEVICE FOR ALLOWING A PERSON TO BE CONNECTED TO AND WALK WITH VARIOUS MEDICAL EQUIPMENT

[76] Inventor: Charles W. Fillon, Jr., 225-3 Pleasant St., Hanson, Mass. 02341

[21] Appl. No.: 09/030,099

[22] Filed: Feb. 25, 1998

[51] Int. Cl.[7] .......................................................... A47F 5/00
[52] U.S. Cl. ..................................... 248/125.7; 348/125.9; 348/415
[58] Field of Search ................................. 248/127, 125.1, 248/165, 125.7, 415, 289.11, 408, 558, 125.9, 158, 159, 425, 900; 403/164, 165, 78, 328

[56] References Cited

U.S. PATENT DOCUMENTS

| | | | |
|---|---|---|---|
| 1,035,100 | 8/1912 | Peterson | 248/159 X |
| 1,589,137 | 6/1926 | Finch | 248/125.9 |
| 2,252,619 | 8/1941 | Clack | 248/159 |
| 2,729,473 | 1/1956 | Warshawsky | 248/289.11 X |
| 4,807,837 | 2/1989 | Gawlik et al. | 248/125.8 |
| 4,821,159 | 4/1989 | Pike | 403/164 X |
| 4,921,190 | 5/1990 | Russo et al. | 248/159 |
| 5,094,418 | 3/1992 | McBarnes, Jr. et al. | 248/286.1 |
| 5,110,076 | 5/1992 | Snyder et al. | 248/125.3 |
| 5,135,191 | 8/1992 | Schmuhl | 248/125.1 |
| 5,188,323 | 2/1993 | David | 248/158 |
| 5,275,364 | 1/1994 | Burger et al. | 248/125.1 |
| 5,337,992 | 8/1994 | Pryor et al. | 248/125.1 |
| 5,366,191 | 11/1994 | Bekanich | 248/125.1 |
| 5,458,305 | 10/1995 | Woodward | 248/121 |
| 5,470,037 | 11/1995 | Willis | 248/125.9 |
| 5,499,644 | 3/1996 | Geniele | 248/159 X |
| 5,603,389 | 2/1997 | Zemon | 182/133 |

*Primary Examiner*—Ramon O. Ramirez
*Assistant Examiner*—Gwendolyn Baxter
*Attorney, Agent, or Firm*—Paul J. Cook

[57] ABSTRACT

The present invention is generally a device for allowing a person to be connected to and walk with various medical equipment (such as an intravenous bag, control system, intravenous hoses and wire). In one embodiment, the device comprises a base member having a plurality of wheels for allowing the device to roll upon a floor. The device further comprises a lower pole member engaged with and extending upward from the base member. The device further comprises an upper pole member and a medical system (such as a intravenous bag, control system, intravenous hose and wires) engaged with and extending outward from the upper pole member and adapted to be connected to the patient. The device further comprises a coupling member engaged with the lower and upper pole members and allowing rotation in either direction and independently of the lower pole member with respect to the upper pole member and/or to allow the upper pole member to remain stationary when the upper pole member is held by the hand by patient. With the device of the present invention, a person may be connected to medical equipment (such as an intravenous bag, control system, intravenous hose and/or wires) and walk and currently push or pull the upper member of the device without the medical equipment (for example, an intravenous bag, control system, intravenous hose and/or wires) becoming entangled with and/or wrapped round the person and/or the device.

8 Claims, 2 Drawing Sheets

DEVICE FOR ALLOWING A PERSON TO BE CONNECTED TO AND WALK WITH VARIOUS MEDICAL EQUIPMENT

FIELD OF THE INVENTION

The present invention relates generally to medical devices. More particularly, the present invention relates to devices for allowing a person to be connected to and walk with various medical equipment such as an intravenous bag and lines.

BACKGROUND OF THE INVENTION

IV poles are well known devices used to allow a person to be connected to and walk with an intravenous bag, control system and intravenous lines. U.S. Pat. No. 5,135,191 discloses one such IV pole. Conventional devices of type exemplified by U.S. Pat. No. 5.125,191 have at least one significant drawback. When the device is connected to a person and is moved along the floor with the person, the intravenous lines often become entangled with and/or wrap around the device and/or person thereby potentially causing harm to the person (for example from a needle pulling out of the person's vein) and/or forcing the person to stop walking and correct the problem and/or require assistance from medical personnel.

The primary object of the present invention is to provide a device that allows a person to be connected to and walk with various medical equipment such as an intravenous bag, control system, and lines without the medical equipment itself preventing the person from walking and/or hurting the person.

SUMMARY OF THE INVENTION

The present invention is generally a device for allowing a person to be connected to and walk with various medical equipment such as an intravenous bag, control system, and lines. In one embodiment, the device comprises a base member having a plurality of wheels for allowing the device to roll upon a floor. The device further comprises a lower pole member engaged with and extending upward from the base member. The device further comprises an upper pole member exending upward. The device further comprises a medical system (such as a intravenous bag, control system, intravenous hose and wires) engaged with and extending outward from the upper pole member and adapted to be connected to the patient. The device further comprises a coupling member engaged with the lower and upper pole members and allowing rotation in either direction and independently of the lower pole member with respect to the upper pole member and/or to allow the upper pole member to remain stationary when the upper pole member is held by the hand by patient. With the device of the present invention, a person may be connected to medical equipment (such as an intravenous bag, control system, intravenous hose and/or wires) and walk and concurrently push or pull the upper member of the device without the medical equipment (for example, an intravenous bag, control system, intravenous hose and/or wires) becoming entangled with and/or wrapped round the person and/or the device.

BRIEF DESCRIPTION OF THE DRAWINGS

The following detailed description of the invention will be better understood with reference to the accompanying drawings in which.

DETAILED DESCRIPTION OF THE PREFERRED EMBODIMENTS

Figure 1:
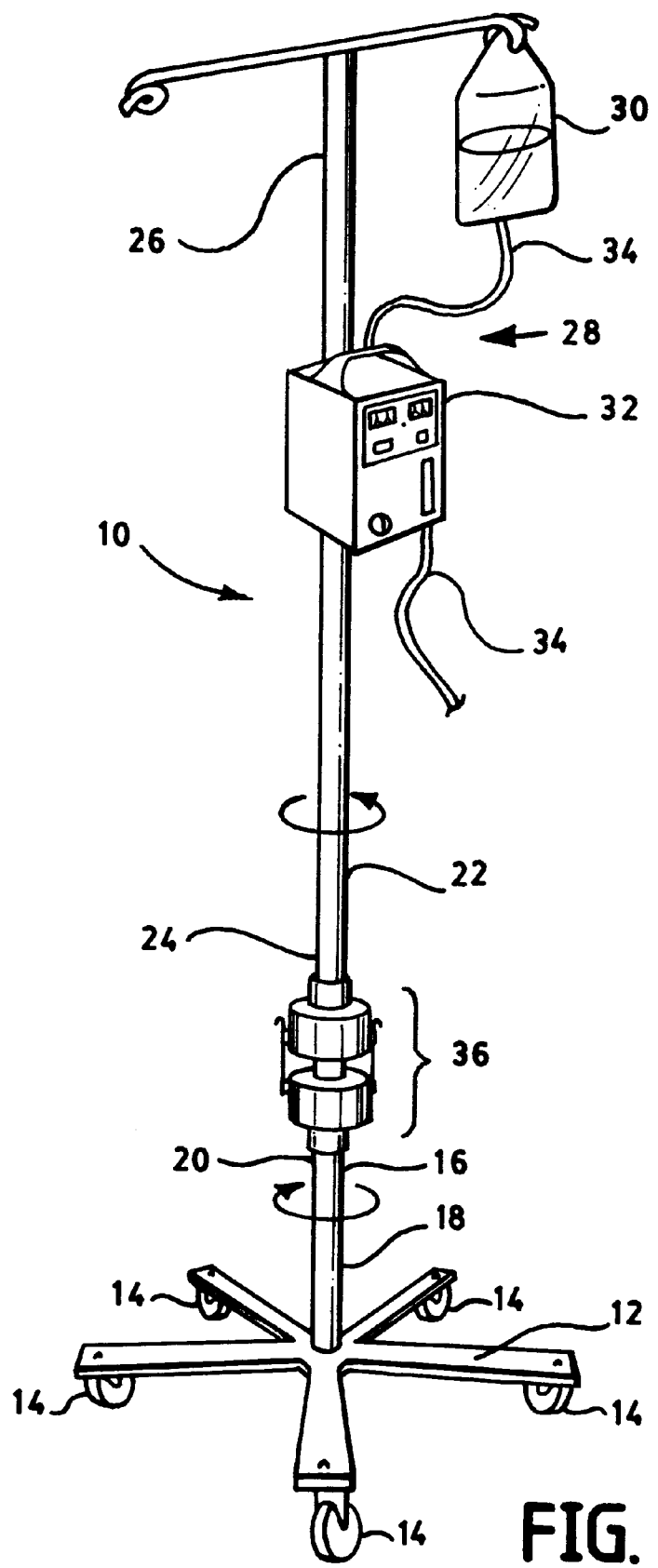
FIG. 1 is perspective view of one embodiment the present invention.

Referring to FIG. 1 where the present invention is as a device 10 which as will be described more fully herein is adapted to allow a person to be connected to and comfortably walk with various medical equipment (such as an intravenous bag, control system, intravenous hoses and wires). In one embodiment the device 10 generally comprises a base member 12 having a plurality of caster wheels 14. The device 10 further comprises a lower member 16 having first and second ends 18 and 20. The first end 18 is engaged with and extending upward from the base member 12. The device 10 further comprises an upper member 22 having first and second ends 24 and 26. The device 10 further comprises a medical system 28 engaged with the upper member 22. The medical system 28 may consist of various medical equipment such as an intravenous bag 30, control unit 32 and intravenous lines 34 and/or wires (not shown). The device 10 further comprises a coupling member 36 which rotatably connects the upper member 22 to the lower member 16.

Figure 2:
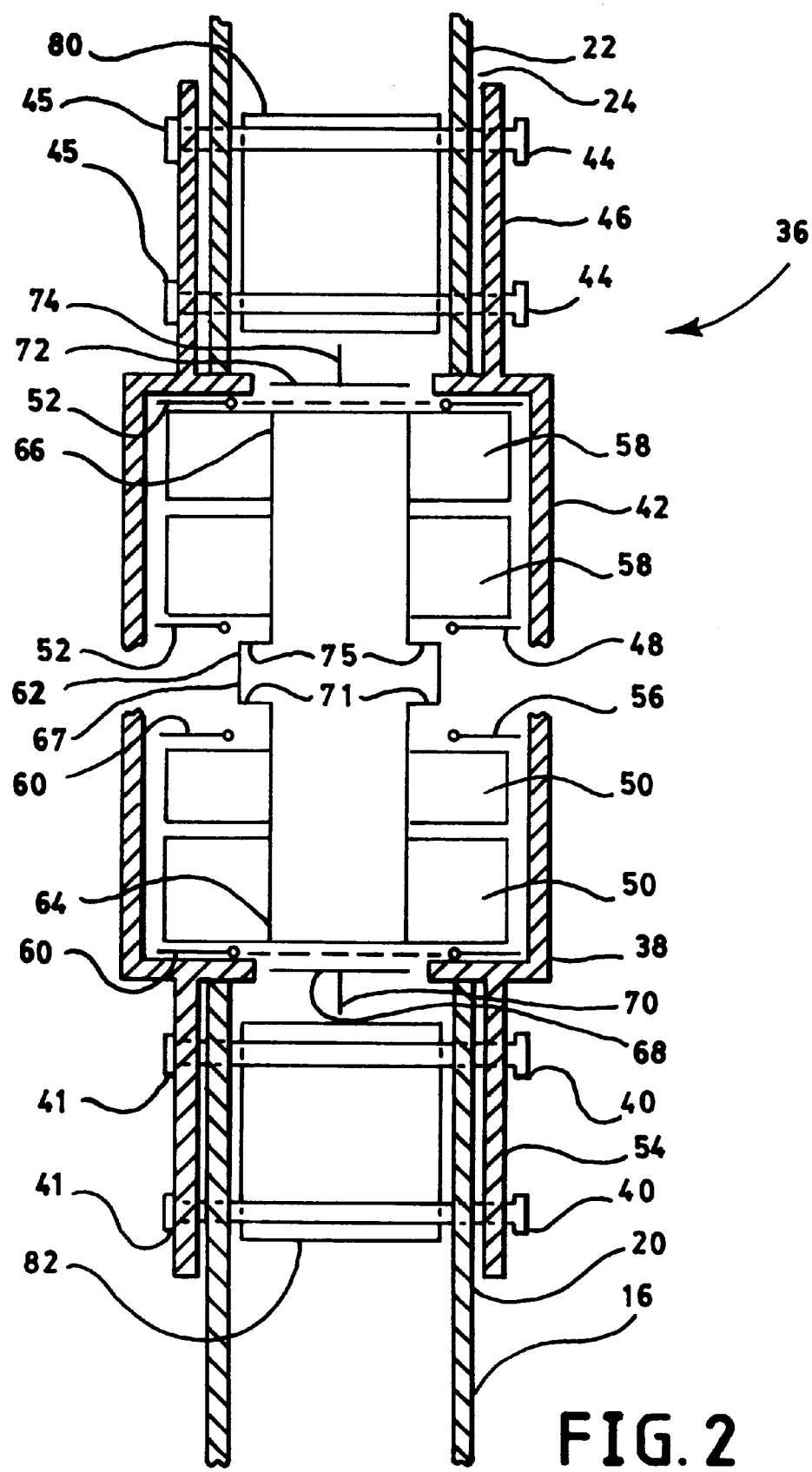
FIG. 2 cross-section view of the first embodiment of the invention.

Referring to FIG. 2, wherein the coupling member 36 generally comprises a lower housing 38 secureably fastened with the second end 20 of the lower member 16 by conventional fastening means such as bolts 40 and nuts 41. The coupling member 36 further comprises an upper housing 42 secureably fastened with the first end 24 of the upper member 22 by conventional fastening means such as bolts 44 and nuts 45. The upper housing 42 comprises a second end 46, a cavity 48, and a bearing assembly 58 disposed and retained within the cavity 48 by conventional fastening means such as a retainer ring(s) 52. The lower housing 38 further comprises a first end 54, a cavity 56, and a bearing assembly 50 disposed and retained within the cavity 56 by conventional fastening means such as a retainer ring(s) 60. The coupling member 36 further comprises an interconnect member 62 such as an elongated shaft having a first end 64 and a second end 66, and a median portion 67 having flanges 71 and 75 extending outward therefrom. Rotatable engagement of the bearing assembly 50 with the first end 64 of the interconnect member 62 is provided by the first end 64 being securely engaged with one side of the bearing assembly 50 by conventional fastening means such as of a cap or flange 68 and a bolt 70 connected to the first end 64 and the opposite side of the bearing assembly 50 being engaged with the flange 71 of the interconnect member 62. Rotatable engagement of the bearing assembly 58 with the second end 66 of the interconnect member 62 is provided by the second end 66 being securely engaged with one side of the bearing assembly 58 by conventional fastening means such as of a cap or flange 72 and a bolt 74 connected to the second end 66 and the opposite side of the bearing assembly 58 being engaged with the flange 75 of the interconnect member 62.

The upper housing 42 and therefore the upper member 22 is rotatable about the interconnect member 62. Likewise, lower housing 38 and therefore the lower member 16 is rotatable about the interconnect member 62. The device 10 of the present invention will alleviate all problems associated with tangling of hoses or wrap around of hoses which are attached to the patient. Use of conventional devices while the patient walks around causes wrap around of hoses or tubes around the pole and/or patient or to become otherwise entangled. As such, with conventional devices a patient can only walk a short distance before the hoses become tangled. Thereafter, the patient would have to stop and unwrap the tangled hoses and/or wires then begin walking again. Conventional devices also have four (4) or five (5) casters on the base which turn and role causing wrap around of the hoses about the middle and/or upper portions of the pole. With the present invention, these problems are eliminated in that rotation of the upper housing 42 and therefore the upper member 22 and/or rotation of the lower housing 38 and therefore the lower member 16 about the interconnect member 62 will prevent and/or significantly reduce the ability of a hose (s) to wrap around the pole as he or she walks and/or as the caster wheels move and/or rotate the device.

The device 10 may further comprise support blocks 80 and 82 disposed within the second end 20 of the lower member 16 and the first end 24 of the upper member 22, respectively, so that upon engagement of bolts 40, 44 and nuts 41 and 45, a secure connection is achieved without deformation of the second end 20 of the lower member 16 and the first end 24 of the upper member 22.

The foregoing description is intended primarily for purposes of illustration. This invention may be embodied in other forms or carried out in other ways without departing from the spirit or scope of the invention. Modifications and variations still falling within the spirit or the scope of the invention will be readily apparent to those of skill in the art.

What is claimed:

1. A device for allowing a person to be connected to and walk with various medical equipment secured to the device, the device comprising:

(a) a base member having a plurality of wheels;

(b) a lower member having first and second ends, said first end being engaged with and extending upward from said base member;

(c) an upper member having first and second ends;

(d) a medical system engaged with said upper member;

(e) a coupling member having first and second end, said coupling member comprising (i) an upper housing comprising a first bearing member engaged with said first end of said upper member (ii) a lower housing comprising a second bearing member engaged with said second end of said lower member and (iii) an interconnect member rotatably engaged with said first bearing member of said lower housing and said second bearing member of said upper housing, and (f) said lower housing comprising an end portion adapted to be engaged with said second end of said lower member and a first cavity portion adapted to receive said first bearing member.

2. The device of claim 1, wherein said upper housing comprises an end portion adapted to engage with said first end of said upper member and a second cavity portion adapted to receive said second bearing member.

3. The device of claim 2, wherein said first bearing member is disposed within said first cavity of said lower housing.

4. The device of claim 3 wherein said second bearing member is disposed within said second cavity of said upper housing.

5. The device of claim 4, wherein said first bearing member is retained within said first cavity of said lower housing by a retainer ring.

6. The device of claim 5 wherein said second bearing member is retained within said second cavity of said upper housing by a retainer ring.

7. The device of claim 6, wherein said first bearing member is engaged with said first end of said interconnect member.

8. The device of claim 7 wherein said second bearing member is engaged with said second end of said interconnect member.

* * * * *